[12] United States Patent
Woo et al.

(10) Patent No.: US 9,841,399 B2
(45) Date of Patent: Dec. 12, 2017

(54) CHEMICAL SENSOR PACKAGE FOR HIGHLY PRESSURED ENVIRONMENT

(71) Applicant: Agency for Science, Technology and Research, Singapore (SG)

(72) Inventors: Daniel Rhee Min Woo, Singapore (SG); How Yuan Hwang, Singapore (SG); Vivek Chidambaram, Singapore (SG); Yuen Sing Chan, Singapore (SG); Eva Leong Ching Wai, Singapore (SG); Jong Bum Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/219,986

(22) Filed: Jul. 26, 2016

(65) Prior Publication Data

US 2017/0003247 A1    Jan. 5, 2017

Related U.S. Application Data

(62) Division of application No. 14/583,261, filed on Dec. 26, 2014, now Pat. No. 9,431,315.

(30) Foreign Application Priority Data

Dec. 26, 2013 (SG) ............................... 201309604-5

(51) Int. Cl.
| | |
|---|---|
| *H01L 23/31* | (2006.01) |
| *G01N 27/414* | (2006.01) |
| *H01L 29/78* | (2006.01) |
| *H01L 29/66* | (2006.01) |
| *H01L 21/56* | (2006.01) |

(Continued)

(52) U.S. Cl.
CPC ............ *G01N 27/414* (2013.01); *H01L 21/56* (2013.01); *H01L 21/565* (2013.01); *H01L 21/76895* (2013.01); *H01L 23/315* (2013.01); *H01L 23/3114* (2013.01); *H01L 23/3135* (2013.01); *H01L 23/481* (2013.01);
(Continued)

(58) Field of Classification Search
CPC ... H01L 23/3114; H01L 21/56; H01L 21/481; H01L 21/3205; H01L 29/788; H01L 29/66477; B81B 7/0061; B81B 7/0048; G01N 27/414; G01L 9/0045
USPC .................................................. 257/416, 253
See application file for complete search history.

(56) References Cited

U.S. PATENT DOCUMENTS 5,632,854 A    5/1997 Mirza et al.
6,548,895 B1 *  4/2003 Benavides .......... H01L 23/4334
                                                            137/594

(Continued)

OTHER PUBLICATIONS

"U.S. Appl. No. 14/583,261, Non Final Office Action dated Jan. 22, 2016", 8 pgs.

(Continued)

*Primary Examiner* — Nathan W Ha
(74) *Attorney, Agent, or Firm* — Schwegman Lundberg & Woessner, P.A.

(57) ABSTRACT

A package for a chemical sensor including an encapsulation and a pressure balancing structure is disclosed. The encapsulation encapsulates a chemical sensor and has a hole for exposing a chemical sensitive part of the chemical sensor. The pressure balancing structure balances pressure applied to the chemical sensor at the chemical sensitive part.

9 Claims, 7 Drawing Sheets

(51) Int. Cl.
*H01L 21/768* (2006.01)
*H01L 23/48* (2006.01)

(52) U.S. Cl.
CPC ........ *H01L 29/66477* (2013.01); *H01L 29/78* (2013.01); *H01L 2924/0002* (2013.01)

(56) References Cited

U.S. PATENT DOCUMENTS

| | | | |
|---|---|---|---|
| 6,790,599 B1 * | 9/2004 | Madou | G01N 27/403 430/311 |
| 9,431,315 B2 | 8/2016 | Woo et al. | |
| 2003/0113979 A1 | 6/2003 | Bieck et al. | |
| 2004/0256349 A1 | 12/2004 | Leib et al. | |
| 2008/0164543 A1 | 7/2008 | Ziglioli et al. | |
| 2009/0082219 A1 | 3/2009 | Ermantraut et al. | |
| 2009/0108382 A1 | 4/2009 | Eriksen et al. | |
| 2009/0278215 A1 | 11/2009 | Baldo et al. | |
| 2011/0192121 A1 | 8/2011 | Kannankeril et al. | |
| 2013/0204227 A1 | 8/2013 | Bochenko et al. | |
| 2013/0269423 A1 | 10/2013 | Angelescu | |
| 2013/0271153 A1 | 10/2013 | Hadwen | |
| 2013/0276544 A1 | 10/2013 | Potasek et al. | |
| 2013/0313452 A1 | 11/2013 | Tice et al. | |
| 2015/0206816 A1 | 7/2015 | Woo et al. | |

OTHER PUBLICATIONS

"U.S. Appl. No. 14/583,261, Notice of Allowance dated May 25, 2016", 7 pgs.

"U.S. Appl. No. 14/583,261, Response filed Apr. 14, 2016 to Non Final Office Action dated Jan. 22, 2016", 9 pgs.

"U.S. Appl. No. 14/583,261, Response filed Nov. 30, 2015 to Restriction Requirement dated Oct. 5, 2015", 6 pgs.

"U.S. Appl. No. 14/583,261, Restriction Requirement dated Oct. 5, 2015", 7 pgs.

* cited by examiner

CHEMICAL SENSOR PACKAGE FOR HIGHLY PRESSURED ENVIRONMENT

PRIORITY CLAIM

This patent application is a Divisional Application and claims the benefit of priority of U.S. patent application Ser. No. 14/583,261, filed on 26 Dec. 2014, which claims the benefit of priority of Singapore Patent Application number 201309604-5 filed on 26 Dec. 2013, the benefit of priority of which is claimed hereby, and which is incorporated by reference herein in its entirety.

FIELD OF THE INVENTION

The invention relates to chemical sensor package. More specifically, the invention relates to chemical sensor package for high pressure environment.

BACKGROUND

Chemical sensors have been used for several areas such as laboratorial or industrial testing and oceanic scientific expedition or oil prospecting. Also, additional encapsulation and packaging is typically required depending on the intended use and application environments.

In some environment such as oceanic applications, high pressure is applied to the chemical sensors and packaging for protecting the chemical sensors from high pressure environment is necessary. For instance, at 3 km below deep sea application, pressure could be increased to 20 kpsi (138 MPa). For the sensor application under such a highly pressurized condition, the pressure differential between the external environment and internal structure of the sensor can be substantial. Existing packaging solutions are unable to withstand such a high pressure difference, limiting their usage for such a high pressure environment.

Thus, what is needed is an improved chemical sensor package that withstands a highly pressurized condition. Furthermore, other desirable features and characteristics will become apparent from the subsequent detailed description and the appended claims, taken in conjunction with the accompanying drawings and this background of the disclosure.

SUMMARY

In a first aspect of the present invention, a package for a chemical sensor including an encapsulation and a pressure balancing structure is disclosed. The encapsulation encapsulates a chemical sensor and has a hole for exposing a chemical sensitive part of the chemical sensor. The pressure balancing structure balances pressure applied to the chemical sensor at the chemical sensitive part.

In a second aspect of the present invention, a method for packaging a chemical sensor is disclosed. The method includes encapsulating a chemical sensor; providing a hole for exposing a chemical sensitive part of the chemical sensor; and providing a pressure balancing structure for balancing pressure applied to the chemical sensor at the chemical sensitive part.

In a third aspect of the present invention, a pressure resistant chemical sensor including a chemical sensor, an encapsulation and a pressure balancing structure is disclosed. The encapsulation encapsulates the chemical sensor and has a hole for exposing a chemical sensitive part of the chemical sensor. The pressure balancing structure balances pressure applied to the chemical sensor at the chemical sensitive part.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with the present embodiment.

FIG. 3, comprising FIG. 3a to FIG. 3c, illustrates simulation models of a bending stress under high pressure loading condition, wherein FIG. 3a illustrate conventional chemical sensor package.

Skilled artisans will appreciate that elements in the figures are illustrated for simplicity and clarity and have not necessarily been depicted to scale. For example, the dimensions of some of the elements in the simulation visualization or steps in the flowcharts may be exaggerated in respect to other elements to help improve understanding of the present embodiment.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present an improved chemical sensor package that withstands in high pressure environment.

Figure 1:
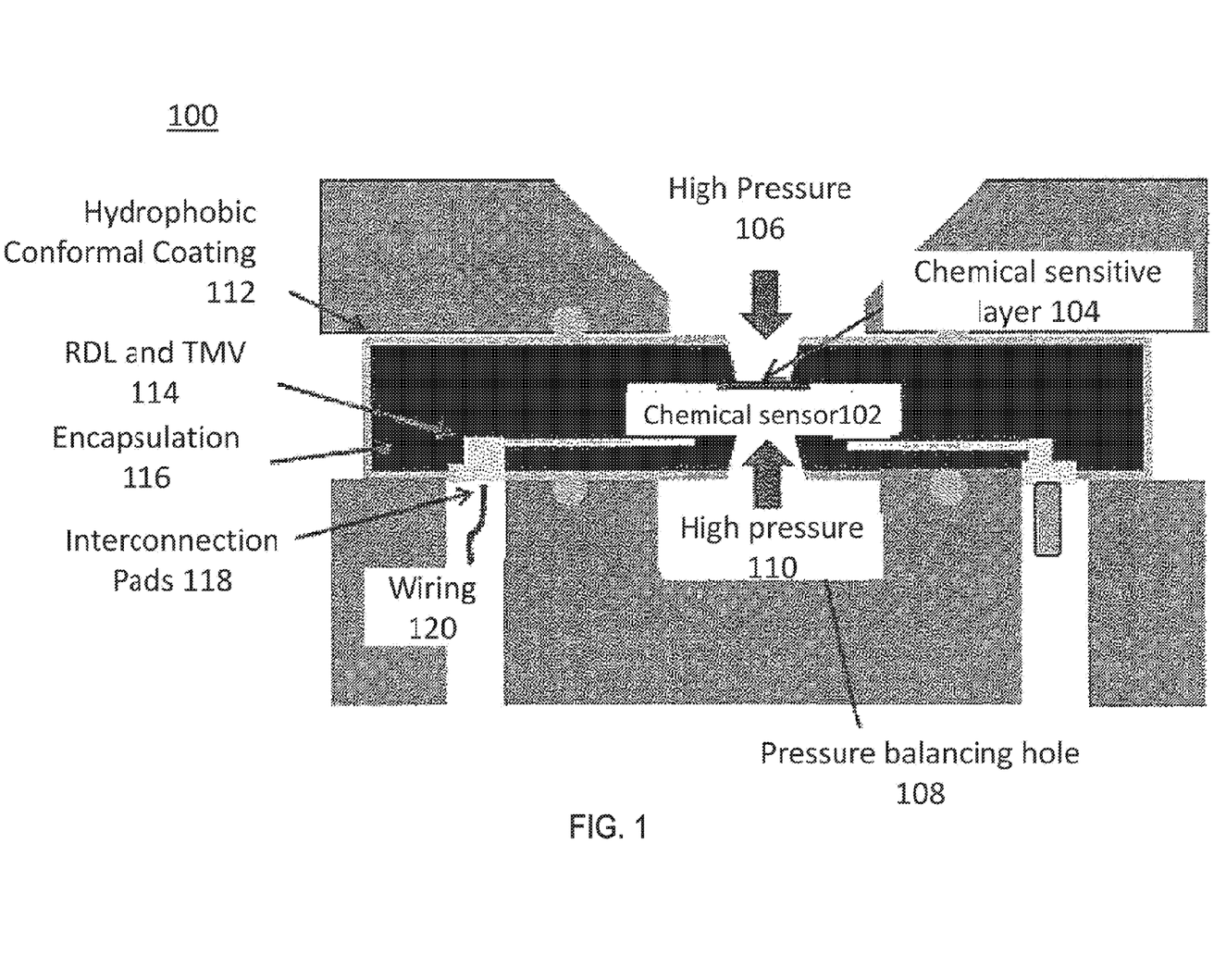
FIG. 1 depicts a chemical sensor package with pressure balancing hole in accordance with a present embodiment.

FIG. 1 depicts a chemical sensor package 100 with pressure balancing hole 108 in accordance with a present embodiment. The chemical sensor package 100 encapsulates chemical sensor 102 by encapsulation 116. However, chemical sensitive layer 104 of chemical sensor 102 is exposed for sensing purpose. When the chemical sensor 102 is under highly pressurized environment, the chemical sensor 102 receives high pressure 106 at the exposed part, i.e. chemical sensitive layer 104. Conventional chemical sensor package without pressure balancing structure is unable to withstand such a high pressure 106.

The chemical sensor package 100 in accordance with a present embodiment has pressure balancing hole 108 to withstand the high pressure 106 by applying counter pressure 110 to the chemical sensor 102 from opposite side of the chemical sensor. Since both sides of the chemical sensor 102 are in direct contact with high pressure environment, the pressure differential experienced by conventional chemical sensor package without pressure balancing structure will be eliminated.

In addition, the chemical sensor package 100 includes a conformal coating 112 for protecting the chemical sensor package 100. The conformal coating 112 may be hydrophobic conformal coating for use in e.g. deep sea application. Such a waterproof coating will enhance reliability of the chemical sensor package 100.

Furthermore, the chemical sensor package 100 includes Redistribution Layer (RDL) 114 on the chemical sensor 102 for moving a wiring 120 outside of the encapsulation 116 away from the opposite side of the chemical sensitive part 104. Since RDL 114 redistributes the wiring 120, counter pressure 110 applied to the chemical sensor 102 will not interfere with the wiring 120. The chemical sensor package 100 further includes Through Mold Via (TMV) interconnection 114 for connecting the chemical sensor 102 to the wiring 120 outside of the encapsulation 116 via interconnection pad 118.

The chemical sensor package 100 is fabricated through fan-out wafer level packaging (FO-WLP) instead of fan-in wafer level packaging (FI-WLP). Enhanced design flexibility of FO-WLP enables to have a pressure balancing structure 108 within the chemical sensor package 100.

Preferably the chemical sensor 102 is an ion sensitive field effect transistor (ISFET) and the chemical sensitive layer 104 is an ion sensitive layer. Ion species detection by the ion sensitive layer is largely dependent upon the type of membrane deposited and is not restricted to detecting only pH ($H^+$ ion). Also the chemical sensor 102 may detect liquid or gas in accordance with appropriate chemical sensing layer 104.

Figure 2:
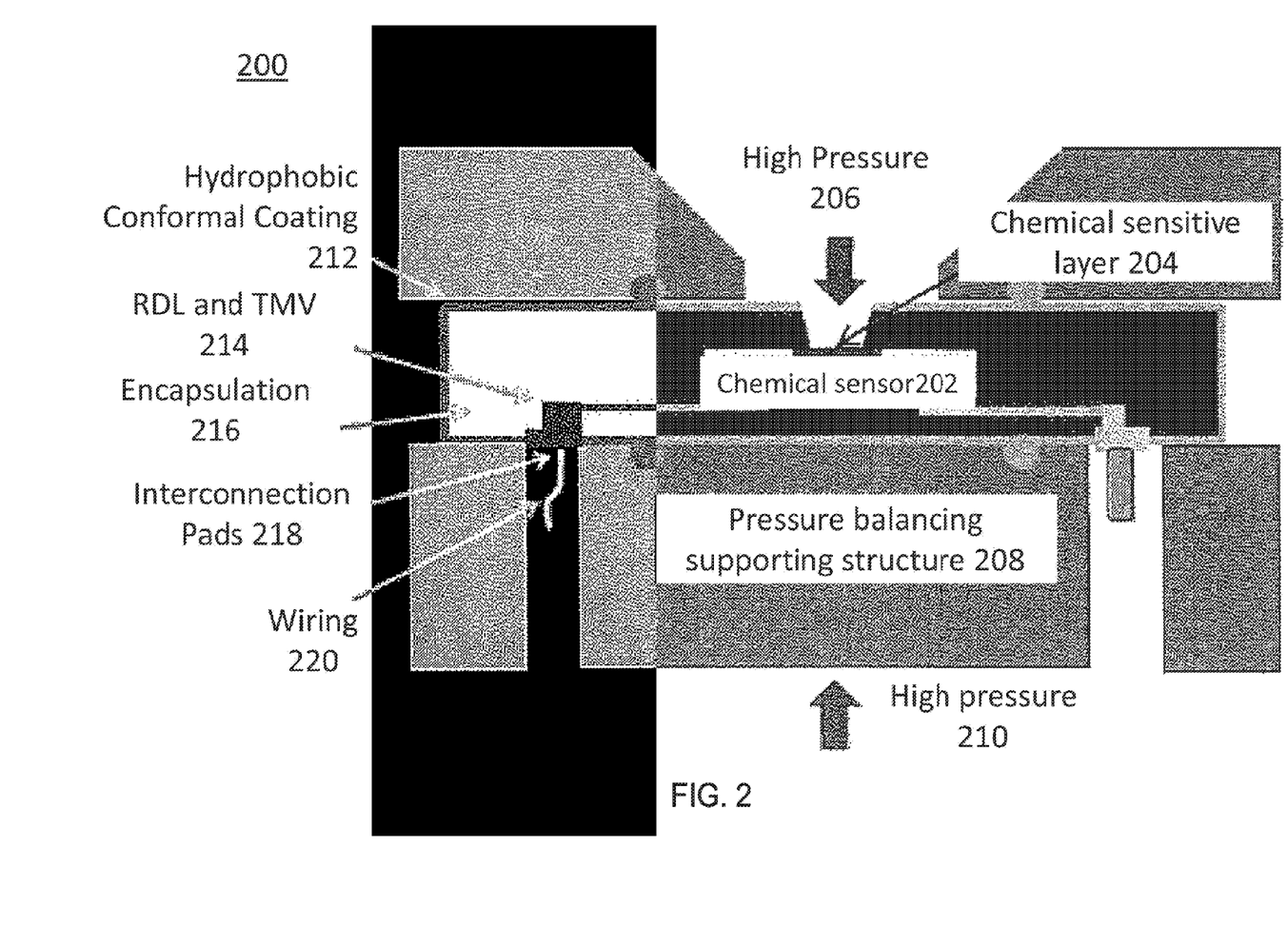
FIG. 2 depicts a chemical sensor package with pressure balancing supporting structure in accordance with a present embodiment.

FIG. 2 depicts a chemical sensor package 200 with pressure balancing supporting structure 208 in accordance with a present embodiment. The chemical sensor package 200 is similar to the chemical sensor package 100 of FIG. 1. The difference is pressure balancing hole 108 is replaced by pressure balancing supporting structure 208. Counter pressure 210 for mitigating high pressure 206 on chemical sensitive layer 204 of the chemical sensor 202 will be applied to chemical sensor 202 via the pressure balancing supporting structure 208.

Similar to chemical sensor package 100 of FIG. 1, the chemical sensor package 200 includes a conformal coating 212 for protecting the chemical sensor package 200. The conformal coating 112 may be hydrophobic conformal coating for use in e.g. deep sea application. Such a waterproof coating will enhance reliability of the chemical sensor package 200.

Furthermore, the chemical sensor package 200 includes Redistribution Layer (RDL) 214 on the chemical sensor 202 for moving a wiring 220 outside of the encapsulation 216 away from the opposite side of the chemical sensitive part 204. Since RDL 214 redistributes the wiring 220, counter pressure 210 applied to the chemical sensor 202 will not interfere with the wiring 220. The chemical sensor package 200 further includes Through Mold Via (TMV) interconnection 214 for connecting the chemical sensor 202 to the wiring 220 outside of the encapsulation 116 via interconnection pad 218.

The chemical sensor package 200 is fabricated through fan-out wafer level packaging (FO-WLP) instead of fan-in wafer level packaging (FI-WLP). Enhanced design flexibility of FO-WLP enables to have a pressure balancing structure 208 within the chemical sensor package 200.

Figure 3A:
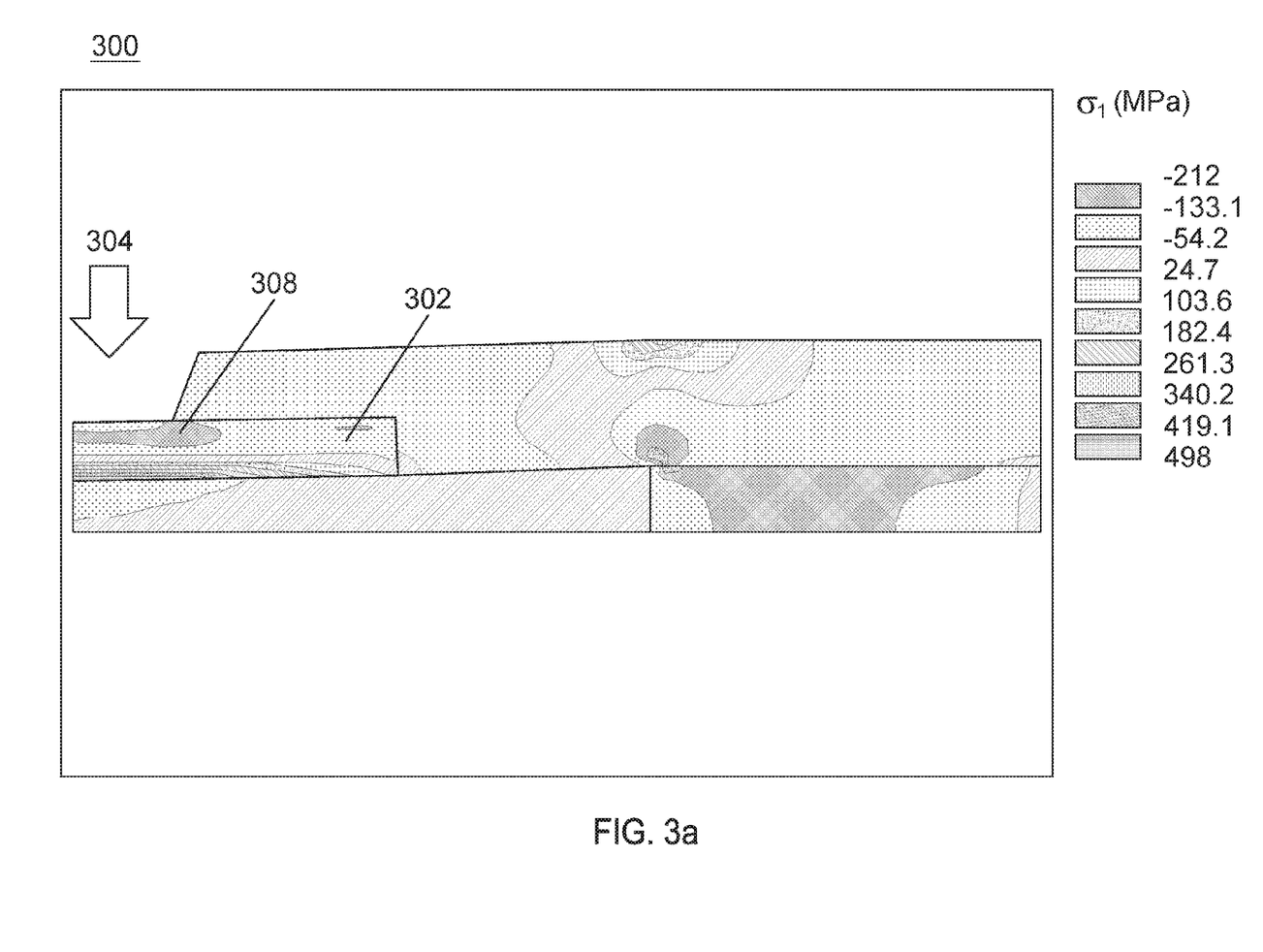
Figure 3B:
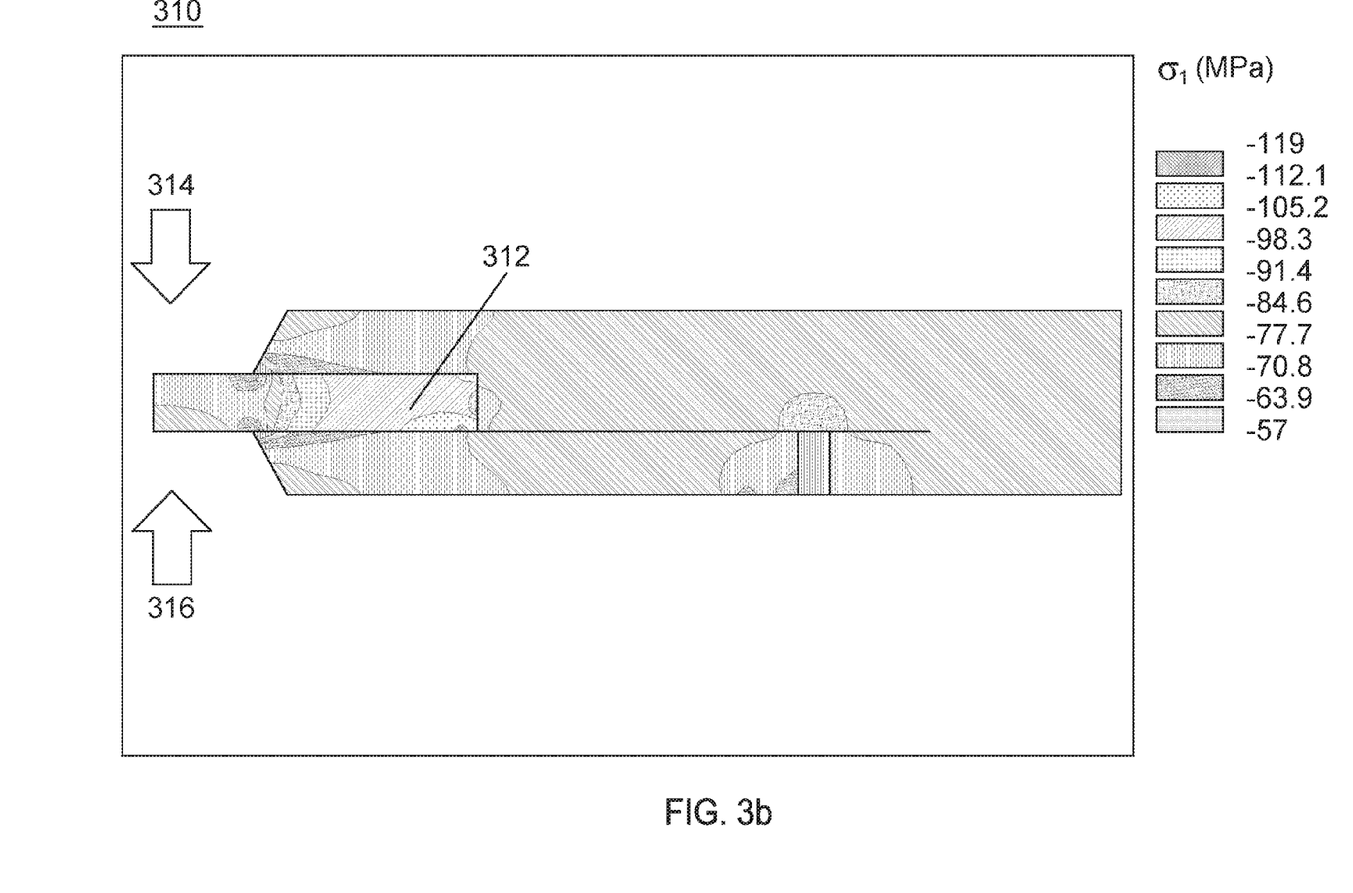
FIG. 3b illustrates a chemical sensor package with pressure balancing hole in accordance with a present embodiment and FIG. 3c illustrates a chemical sensor package with pressure balancing supporting structure in accordance with a present embodiment.
Figure 3C:
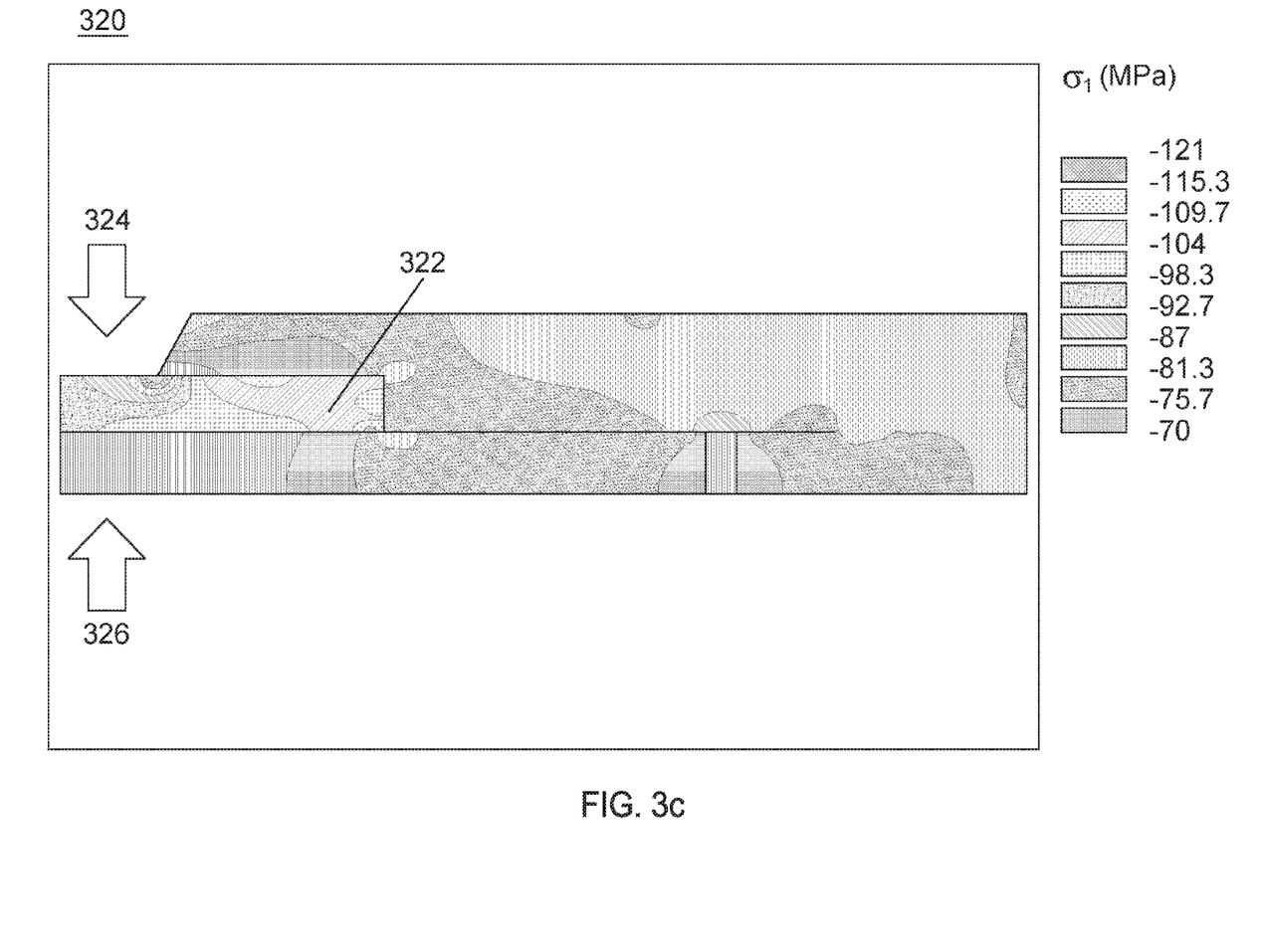

FIGS. 3a, 3b and 3c depict bending stress simulation models. In the simulation models, a 20 kpsi pneumatic pressure loading is applied to simulate the high pressure loading condition for deep sea environment for the estimated depth as 3 km.

FIG. 3a depicts bending stress simulation model 300 of conventional chemical sensor package. The conventional chemical sensor package does not have pressure balancing structure. Due to the asymmetrical configuration, chemical sensor 302 experiences a heavy stress distortion as well as a bending stress (498 MPa) that exceeded the flexural strength of Silicon at the highly stressed point 308 by high pressure 304.

On the other hand, FIG. 3b depicts bending stress simulation model 310 of chemical sensor package with pressure balancing hole in accordance with a present embodiment. Aside from the symmetrical configuration which can eliminate stress distortion and bending on the chemical sensor 312 by cancelling high pressure 314 with counter high pressure 316, the maximum stress experienced by the chemical sensor 312 turned out to be only compressive component with low stress level (−57 MPa).

Also, FIG. 3c depicts bending stress simulation model 320 of chemical sensor package with pressure balancing supporting structure in accordance with a present embodiment. Similar to FIG. 3b, high pressure 324 applied to chemical sensor 322 is cancelled by counter pressure 326. The simulation model 320 shows much lower stress level (−70 MPa) than model of conventional package as shown in FIG. 3a.

Figure 4:
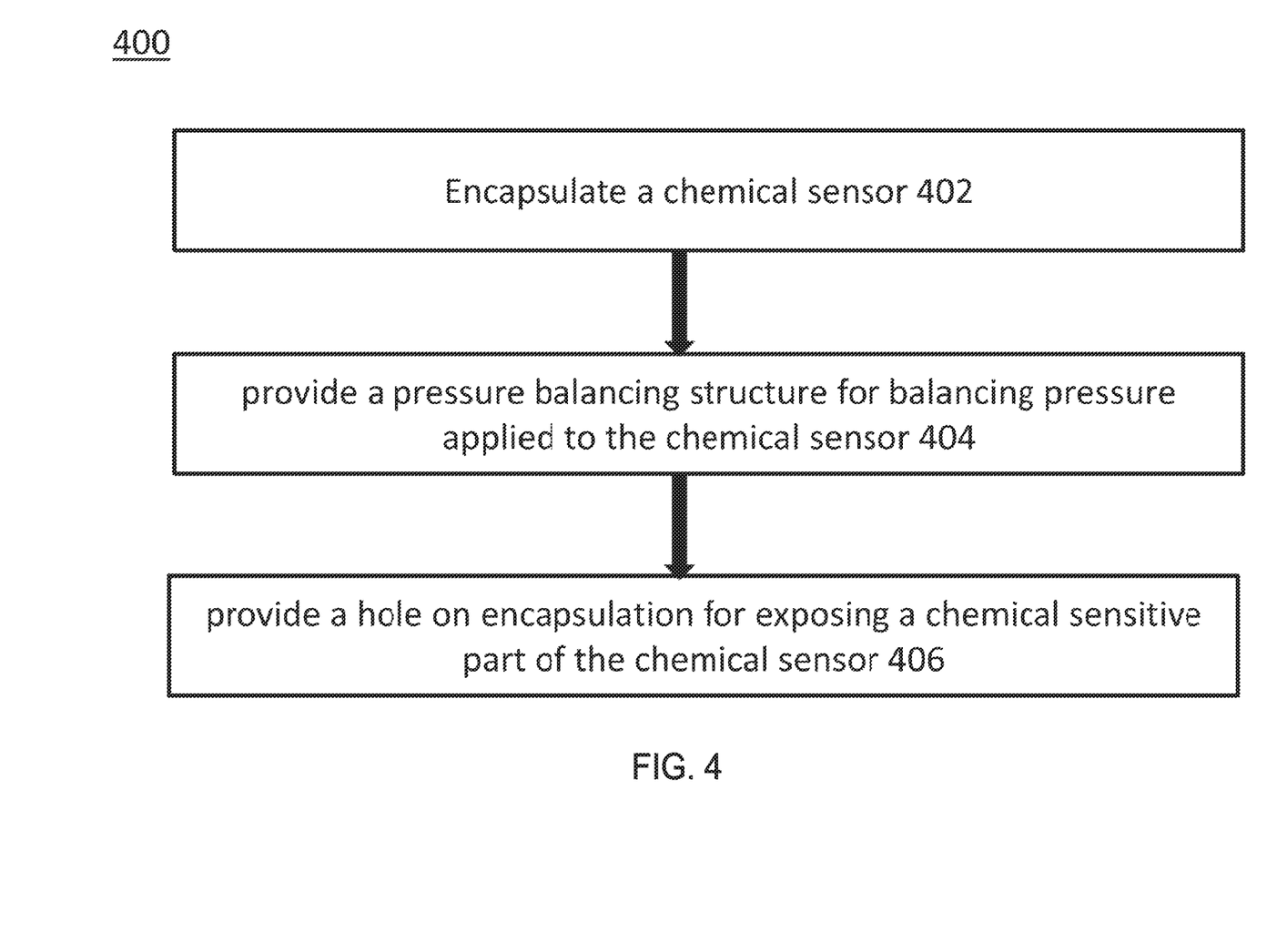
FIG. 4 depicts a flowchart of a method for packaging a chemical sensor in accordance with a present embodiment.

FIG. 4 depicts a flowchart 400 of a method for packaging a chemical sensor in accordance with a present embodiment. In step 402, a chemical sensor is encapsulated by an encapsulation. In step 404, a pressure balancing structure is provided. The pressure balancing structure is balancing pressure applied to the chemical sensor. In step 406, a hole is provided on the encapsulation. The hole exposes a chemical sensitive part of the chemical sensor.

Figure 5:
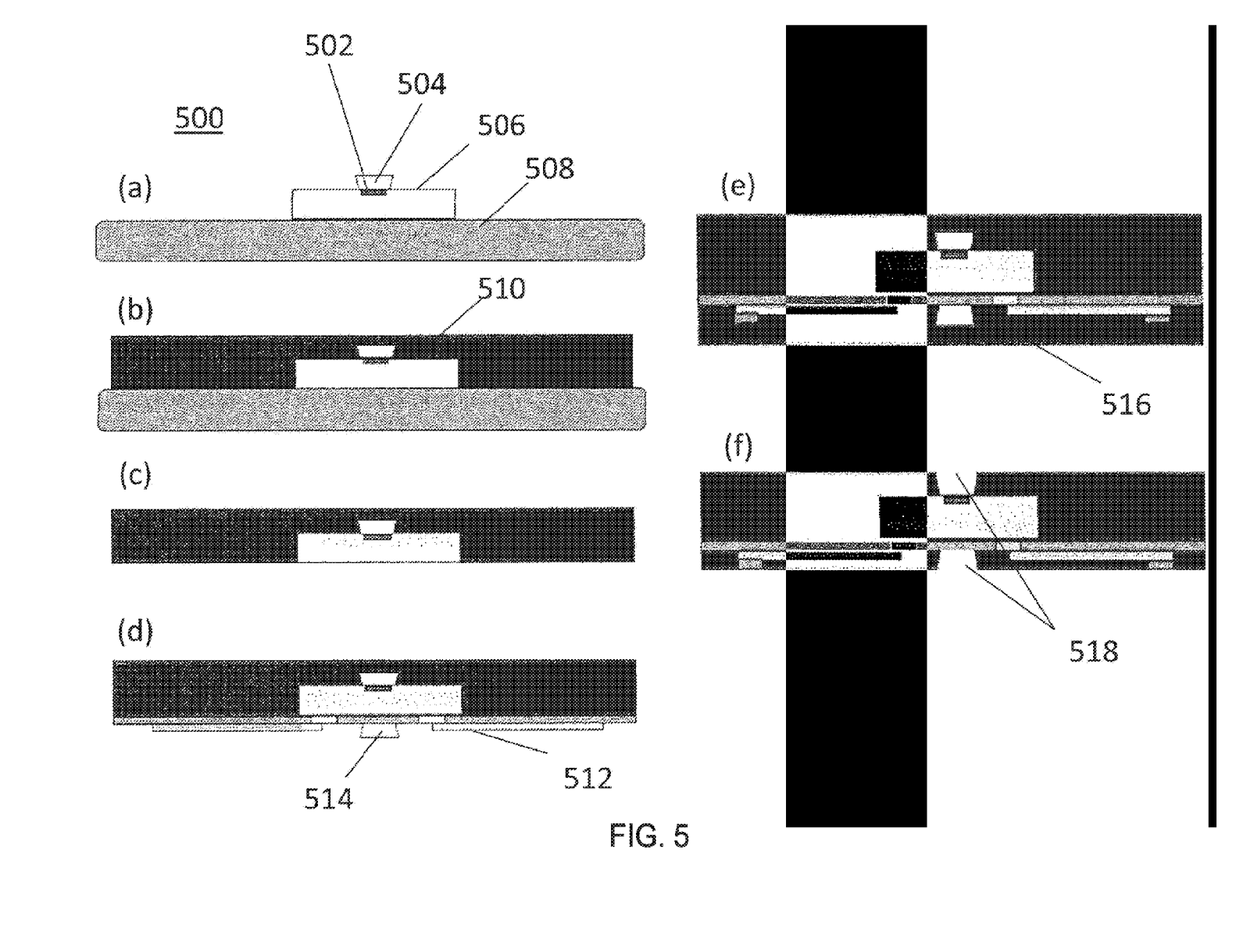
FIG. 5 depicts a detailed packaging flow in accordance with a present embodiment.

FIG. 5 depicts a detailed packaging flow 500 in accordance with a present embodiment. In step (a), a chemical sensor 506 is placed on a carrier 508. Also, a chemical sensitive layer 502 of the chemical sensor 506 is covered by a cap 504 for protection.

In step (b), compression molding is applied to the chemical sensor 506 using encapsulation 510. Since cap 504 is covering chemical sensitive layer 502 of the chemical sensor 506, encapsulation 510 covers the cap 504 instead of chemical sensitive layer 502. In step (c), a carrier 508 is debonded from the chemical sensor 506 and its encapsulation 510.

And then, in step (d), Redistribution Layer (RDL) 512 is provided on the chemical sensor 506. If pressure balancing structure is a pressure balancing hole, further cap 514 is provided on the opposite side of the cap 504 so that symmetrical structure to balance pressure is achieved.

In step (e), interconnection is provided and RDL 512 is encapsulated by further encapsulation 516. In step (f), holes 518 are provided on the position of the cap 504 and the further cap 514. One of the holes 518 exposes the chemical sensitive layer 502 of the chemical sensor 506. The other hole is located the opposite side of the chemical sensor 506 and making symmetrical structure to mitigate high pressure from outside.

While exemplary embodiments have been presented in the foregoing detailed description of the invention, it should be appreciated that a vast number of variations exist. For example, those skilled in the art will realize from the teachings herein that the present technology may also be applied to any part in the other type of chemical sensors.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention. It being understood that various changes may be made in the function and arrangement of elements and method of operation described in an exemplary embodiment without departing from the scope of the invention as set forth in the appended claims.

REFERENCE NUMERALS

100 Chemical sensor package with pressure balancing hole
102 Chemical sensor
104 Chemical sensitive layer
106 High pressure
108 Pressure balancing hole
110 High pressure
112 Hydrophobic Conformal Coating
114 RDL and TMV
116 Encapsulation
118 Interconnection Pads
120 Wiring
200 Chemical sensor package with pressure balancing supporting structure
202 Chemical sensor
204 Chemical sensitive layer
206 High pressure
208 Pressure balancing supporting structure
210 High pressure
212 Hydrophobic Conformal Coating
214 RDL and TMV
216 Encapsulation
218 Interconnection Pads
220 Wiring
300 Bending stress simulation model of conventional chemical sensor package
302 Chemical sensor
304 High pressure
308 Highly stressed point
310 Bending stress simulation model of chemical sensor package with pressure balancing hole
312 Chemical sensor
314 High pressure
316 High pressure
320 Bending stress simulation model of chemical sensor package with pressure balancing supporting structure
322 Chemical sensor
324 High pressure
326 High pressure
400 Flowchart of a method for packaging a chemical sensor
402 Encapsulate a chemical sensor
404 Provide a pressure balancing structure for balancing pressure applied to the chemical sensor
406 Provide a hole on encapsulation for exposing a chemical sensitive part of the chemical sensor
500 Detailed packaging flow
502 Chemical sensitive layer
504 Cap
506 Chemical sensor
508 Carrier
510 Encapsulation
512 Redistribution Layer (RDL)
514 Cap
516 Encapsulation
518 Hole

What is claimed is:

1. A method for packaging a chemical sensor comprising:
providing a chemical sensor having a chemical sensitive area on a first side thereof;
encapsulating the first side of the chemical sensor by an encapsulation;
forming a hole in the encapsulation for exposing the chemical sensitive area of the chemical sensor; and
forming a pressure balancing structure on a second side of the chemical sensor for balancing pressure applied to the chemical sensor at the chemical sensitive area, the second side of the chemical sensor opposite the first side of the chemical sensor.

2. The method in accordance with claim 1, wherein forming the pressure balancing structure comprises encapsulating the second side of the chemical sensor by a further encapsulation wherein the encapsulating comprises forming a pressure balancing hole for applying counter pressure to the second side of the chemical sensor opposite the chemical sensitive part, the method further comprising forming a Redistribution Layer (RDL) on the chemical sensor for moving a wiring away from the pressure balancing hole.

3. The method in accordance with claim 1, wherein forming, the pressure balancing structure comprises forming a pressure balancing supporting structure on the second side of the chemical sensor for applying counter pressure to the second side of the chemical sensor opposite the chemical sensitive part, the method further comprising providing a Redistribution Layer (RDL) on the chemical sensor for moving a wiring away from the pressure balancing supporting structure opposite the chemical sensitive part.

4. The method in accordance with claim 2, further comprising forming a Through Mold Via (TMV) interconnection for connecting the chemical sensor to the wiring.

5. The method in accordance with claim 1, wherein the package is fabricated through fan-out wafer level packaging (FO-WLP) process.

6. The method in accordance with claim 1, further comprising coating the encapsulation by a hydrophobic conformal coating.

7. The method in accordance with claim 3, further comprising forming a Through Mold Via (TMV) interconnection for connecting the chemical sensor to the wiring.

8. The method in accordance with claim 1, wherein encapsulating the first side of the chemical sensor comprises:
covering the chemical sensitive area on the first side of the chemical sensor with a cap;
encapsulating the first side of the chemical sensor by the encapsulation; and
removing the cap to form the hole in the encapsulation for exposing the chemical sensitive part of the chemical sensor.

9. The method in accordance with claim 2, wherein encapsulating the second side of the chemical sensor comprises:
covering a portion of the second side of the chemical sensor opposite the chemical sensitive area with a cap;
encapsulating the second side of the chemical sensor by the further encapsulation; and removing the cap to form the pressure balancing hole for applying counter pressure to the second side of the chemical sensor opposite the chemical sensitive part.

* * * * *